(12) United States Patent
Harvey et al.

(10) Patent No.: US 9,370,775 B2
(45) Date of Patent: Jun. 21, 2016

(54) CONTROLLED TRANSFER BIOLOGICAL SAMPLE COLLECTION DEVICES AND METHODS OF USING SUCH DEVICES

(71) Applicant: GE HEALTHCARE BIO-SCIENCES CORP., Piscataway, NJ (US)

(72) Inventors: Michael A. Harvey, Spofford, NH (US); Breck Olland Parker, Saco, ME (US); Stevan Paul Tortorella, Wells, ME (US); Elizabeth A. Moran, Randolph, NJ (US); John Pipinias, Elliot, ME (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 0 days.

(21) Appl. No.: 13/923,789

(22) Filed: Jun. 21, 2013

(65) Prior Publication Data

US 2014/0000392 A1    Jan. 2, 2014

Related U.S. Application Data

(63) Continuation of application No. 12/449,603, filed as application No. PCT/GB2008/000542 on Feb. 15, 2008, now Pat. No. 8,468,901, which is a continuation of application No. 11/707,313, filed on Feb. 16, 2007, now Pat. No. 7,748,283.

(51) Int. Cl.
*B01L 9/00* (2006.01)
*B01L 3/00* (2006.01)
(Continued)

(52) U.S. Cl.
CPC . *B01L 9/00* (2013.01); *B01L 3/505* (2013.01); *B01L 3/5023* (2013.01); *G01N 1/02* (2013.01);
(Continued)

(58) Field of Classification Search
CPC . B01L 3/5023; B01L 2300/043; B01L 3/505; B01L 3/5055; B01L 9/00; G01N 1/02; G01N 2001/028; G01N 33/54366
USPC ............... 73/864.31, 863.32, 864.51, 764.71, 73/864.91
See application file for complete search history.

(56) References Cited

U.S. PATENT DOCUMENTS 2,905,169 A * 9/1959 Nieburgs ...................... 600/572
3,996,006 A    12/1976 Pagano
(Continued)

FOREIGN PATENT DOCUMENTS

JP    2006232686    8/2006

OTHER PUBLICATIONS

Office Action Dated May 23, 2014 Issued on Corresponding JP Patent Application No. 2013-125678.

*Primary Examiner* — Peter Macchiarolo
*Assistant Examiner* — Natalie Huls
(74) *Attorney, Agent, or Firm* — Sutherland Asbill & Brennan LLP

(57) ABSTRACT

The field of the present invention pertains to a controlled transfer biological collection device using a dry solid storage and transfer medium and a method for the collection of biological material of interest (genetic or proteinaceous material) in a form suitable for storage and/or subsequent analysis. Specifically, the present invention provides for a sampling device that controls the transfer of the biological sample to the storage medium by holding the storage medium and a moveable sample collection member having an analyte collection surface. The invention further provides for a method not only for storing a biological analyte on this collection device but also for analyzing the stored biological analyte using methods that are suited for automated analyzing systems.

7 Claims, 11 Drawing Sheets

(51) Int. Cl.
*G01N 1/02* (2006.01)
*G01N 35/00* (2006.01)

(52) U.S. Cl.
CPC ...... *B01L 2200/027* (2013.01); *B01L 2300/069* (2013.01); *G01N 2001/028* (2013.01); *G01N 2035/00356* (2013.01)

(56) References Cited

U.S. PATENT DOCUMENTS

| | | | |
|---|---|---|---|
| 4,645,743 A | 2/1987 | Baker et al. | |
| 4,789,629 A | 12/1988 | Baker et al. | |
| 4,963,325 A * | 10/1990 | Lennon et al. | 422/408 |
| 5,308,580 A | 5/1994 | Clark | |
| 5,418,142 A | 5/1995 | Kiser et al. | |
| 5,756,126 A | 5/1998 | Burgoyne | |
| 5,766,962 A * | 6/1998 | Childs et al. | 436/518 |
| 5,939,259 A | 8/1999 | Harvey et al. | |
| 5,972,386 A | 10/1999 | Burgoyne | |
| 5,976,572 A | 11/1999 | Burgoyne | |
| 5,980,828 A | 11/1999 | McClintock et al. | |
| 6,168,922 B1 | 1/2001 | Harvey et al. | |
| 6,294,203 B1 | 9/2001 | Burgoyne | |
| 6,447,804 B1 | 9/2002 | Burgoyne | |
| 6,627,226 B2 | 9/2003 | Burgoyne et al. | |
| 7,195,878 B2 * | 3/2007 | Cleator | 435/6.19 |
| 7,311,671 B2 * | 12/2007 | Jung et al. | 600/562 |
| 7,488,450 B2 | 2/2009 | Matusewicz et al. | |
| 8,998,824 B2 * | 4/2015 | Pierce | A61B 10/0045 600/572 |
| 2001/0039057 A1 | 11/2001 | Douglas et al. | |
| 2004/0116826 A1 * | 6/2004 | Jung et al. | 600/562 |
| 2004/0161855 A1 * | 8/2004 | Kvasnik et al. | 436/174 |
| 2005/0196318 A1 | 9/2005 | Matusewicz et al. | |
| 2005/0227269 A1 | 10/2005 | Lloyd, Jr. et al. | |
| 2006/0057738 A1 | 3/2006 | Hall, Jr. | |
| 2006/0246598 A1 | 11/2006 | Dai et al. | |
| 2013/0344616 A1 * | 12/2013 | Triva | 436/174 |
| 2014/0100480 A1 * | 4/2014 | Pierce et al. | 600/573 |

* cited by examiner

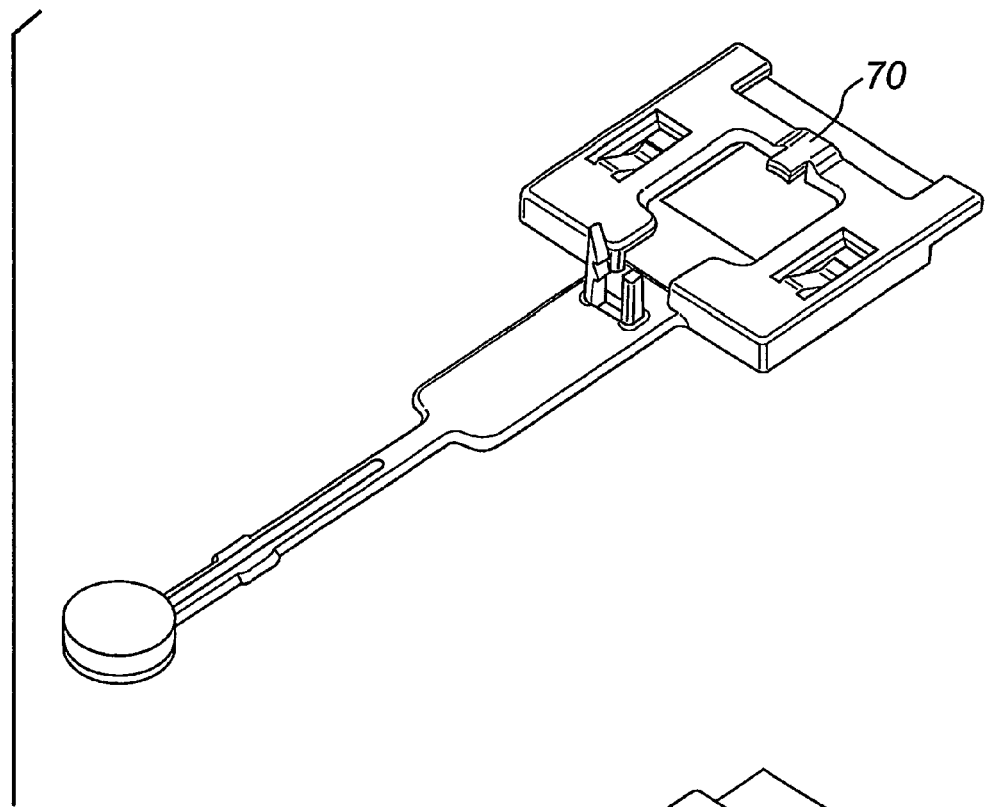
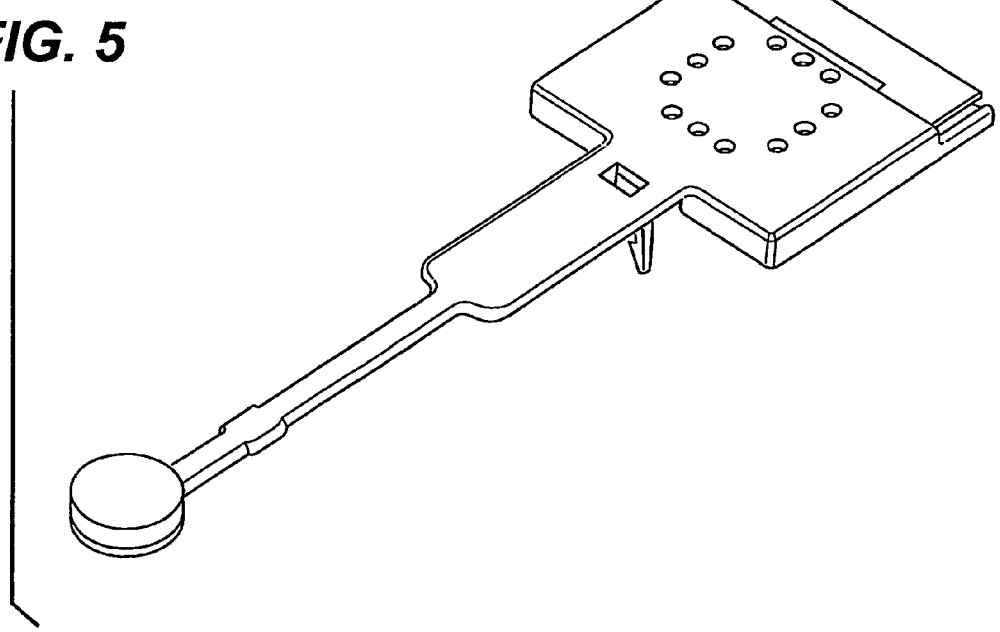
FIG. 5

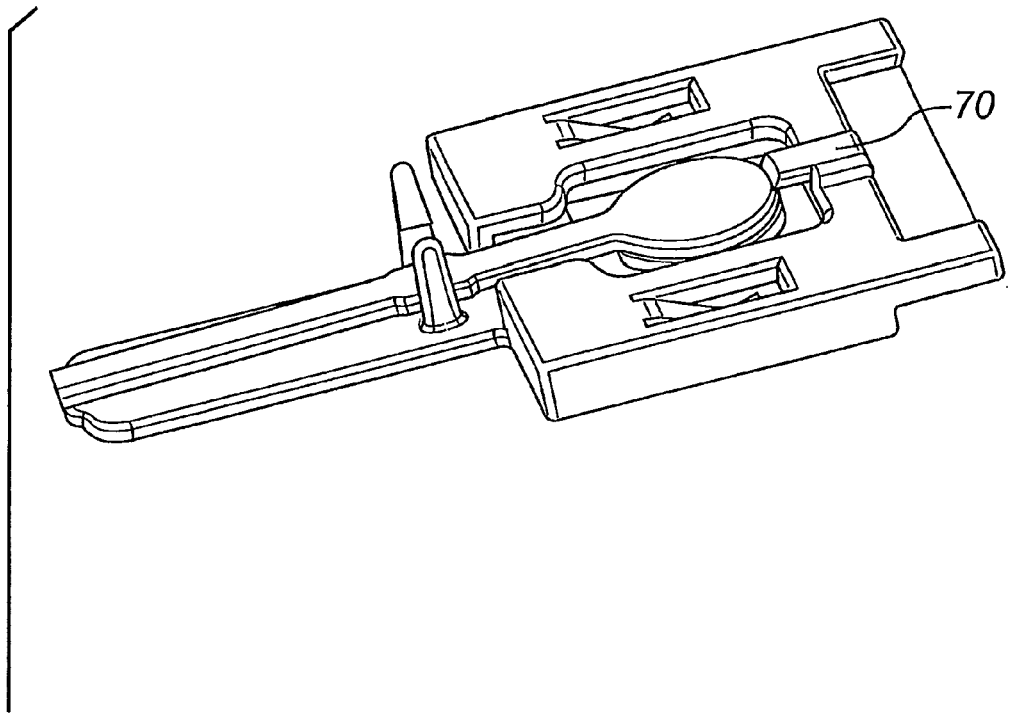
FIG. 6
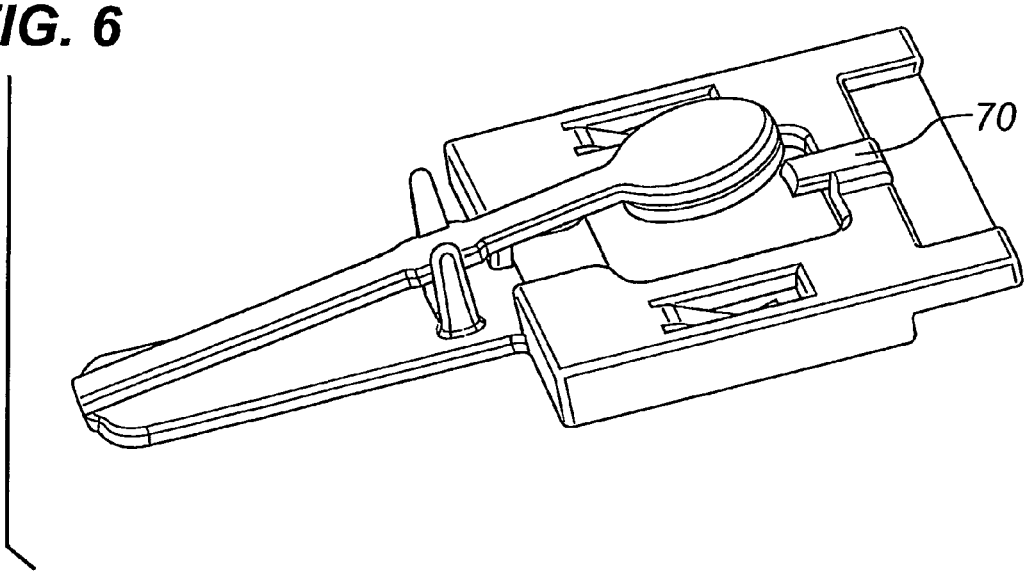

CONTROLLED TRANSFER BIOLOGICAL SAMPLE COLLECTION DEVICES AND METHODS OF USING SUCH DEVICES

CROSS-REFERENCES TO RELATED APPLICATIONS

The present application is a continuation-in-part application of U.S. Ser. No. 11/707,313, filed Feb. 16, 2007, the disclosure of which is incorporated herein by reference.

BACKGROUND OF THE INVENTION (1) Field of the Invention

The field of the present invention pertains to a controlled transfer biological collection device using a dry solid storage and transfer medium and a method for the collection of biological material of interest (genetic or proteinaceous material) in a form suitable for storage and/or subsequent analysis. Specifically, the present invention provides for a sampling device that controls the transfer of the biological sample to the storage medium by holding the storage medium and a moveable sample collection member having an analyte collection surface. The invention further provides for a method not only for storing a biological analyte on this collection device but also for analyzing the stored biological analyte using methods that are suited for automated analyzing systems.

(2) Description of the Related Art, Including Information Disclosed Under 37 CFR 1.97 & 1.98

The collection of biological samples (such as blood) and extracting DNA for genetic analysis from the sample has been widely used by the forensics and medical community for identification purposes, for paternity testing, for genetic diagnostic testing in new born screening programs, for genetic typing for predisposition to disease and for genetic characterization for drug susceptibility. However, due to the invasive nature of blood collection, alternative non-invasive methods are coming into favor. Current methods involve scraping cellular mucosa from inside the oral cavity using any of a number of different devices such as cytobrushes, cotton or Dacron swabs, mouthwash swish and rinse methods, foam tipped swabs, and supported cellulosic filter paper collection techniques (known as the Bode method). These methods require time-consuming, labor intensive extraction methods.

The introduction of treated storage matrices into the forensics community has significantly streamlined the collection and extraction of DNA from a variety of samples. The use of FTA® brand treated matrices (from Whatman, Inc. of Florham Park, N.J. USA) with non-invasive buccal cell collection techniques presents a new set of problems. With the use of conventional buccal swabs, one can fail to transfer buccal cells to the treated matrix in a consistent and reproducible manner. If the swab used to collect the sample is separate and distinct from the treated matrix receiving the sample, then forensic traceability issues arise, particularly if the two become separated later in the chain of custody of forensic evidence.

Examples of treated matrices for biological sample collection or storage and associated collection devices can be found in the following US patents: U.S. Pat. No. 6,627,226, U.S. Pat. No. 6,447,804, U.S. Pat. No. 6,294,203, U.S. Pat. No. 6,168,922, U.S. Pat. No. 5,976,572, U.S. Pat. No. 5,972,386, U.S. Pat. No. 5,939,259, and U.S. Pat. No. 5,756,126. Basically, these patents use two different methodologies for stabilizing biological samples.

The first stabilizing method uses a combination of an absorbent material as a storage medium that does not bind to nucleic acids and a chaotropic salt impregnated about the storage medium. (For the purposes of the cited prior art and the present invention, "chaotropic salts" include any substance capable of altering the secondary, tertiary, or quaternary structure of biomolecules in aqueous solution, but leaves the primary structure intact.) Preferably, a chaotropic salt is said to inactivate any nucleic acid amplification inhibitors present in the biological source, by precipitation, by inducing the inhibitor to irreversibly bind to the matrix, or by causing substantially irreversible denaturation of the inhibitor. Suitable chaotropic salts include guanidinium salts such as guanidine isothiocyanate, guanidine thiocyanate, guanidine hydrochloride, sodium iodide, sodium perchlorate, potassium iodide, sodium isothiocyanate, urea, or combinations thereof.

The second stabilizing method also uses a dry solid storage medium but a different adsorbed or absorbed stabilizer. Here, the protectant composition comprises a protein denaturing agent (such as an anionic detergent) and a free radical trap (such as a weak base, and a chelating agent, and optionally, uric acid or a urate salt).

BRIEF SUMMARY OF THE INVENTION

The present invention relates to a controlled transfer biological collection device using a dry solid storage and transfer medium and a method for the collection of biological material of interest (genetic or proteinaceous material) in a form suitable for storage and/or subsequent analysis.

The present collection device for a biological sample that contains degradable biologically sourced analytes comprises three elements. A moveable sample collection member is one element and is equipped with an analyte collection surface that, preferably, has the ability to absorb more sample than is necessary for transfer to a storage medium. A storage medium suitable for collecting and storing the biological sample is held in place by a storage medium holder. The holder not only keeps the operator's fingers away from the storage transfer location, but also provides a holding means for holding the storage medium in a fixed position and for applying contact pressure between the storage medium and the analyte collection surface. The holder also has a means for holding the moveable sample collection member. Thus, the two elements, the storage medium and the analyte collection surface are held together for traceability purposes.

Functionally, the moveable sample collection holding means allows the moveable collection member, and its analyte collection surface, to move between a first open position for collecting the biological sample on the analyte collection surface prior to sample collection and a second closed position facing or contacting at least a portion of the storage medium after collection and transfer of the sample. For the purposes of the present invention, the term "surface" refers to more than a two-dimensional space, including volume as well. Thus, a "surface" can be the volume of a foam pad, for example, and not just its contact surface area.

In use, one takes the above described device and contacts the analyte collection surface with the biological sample. The moveable collection member is moved towards the storage medium such that the analyte collection surface and the storage medium are brought in contact, allowing the transfer of the biological sample to the storage medium. In preferred embodiments, one engages the holding means on the storage medium holder in doing so, thereby allowing the analyte collection surface to be held facing the storage medium after the transfer is complete.

Preferably, the means for holding the moveable sample collection member comprises a resilient member, which may be molded into the storage medium holder. In one embodiment, the resilient member is such that, in use, it engages the moveable collection member and releasably holds it in a fixed position such that the surface of the moveable collection member is in contact with the storage medium, thereby maintaining a uniform and constant pressure between the moveable collection member surface and the storage medium. Preferably the pressure is sufficient to facilitate the transfer of the biological sample from the analyte collection surface of the moveable sample collection member to the storage medium. The person skilled in the art will be able to determine the relative position of the resilient member which is required in order to ensure sufficient transfer of the biological sample from the analyte collection surface of the moveable sample collection member to the storage medium.

For analysis of the biological sample, the storage medium is manipulated so as to remove at least a portion of the biologically sourced analyte present on the storage medium.

Examples of storage media suitable for the present invention include untreated filter paper, such as #903® brand paper (Whatman, Inc., Florham Park, N.J. USA) or treated filter papers, such as FTA and FTA Elute brand paper (also from Whatman, Inc., Florham Park, N.J. USA). These treated matrices are described in US patents referenced above. Such treated matrices provide a simple safe method for collection, shipping and storage of biological samples. They also contain chemistries which make it easy to isolate DNA from complex samples such as blood. Samples collected on treated or untreated matrices are dried for storage and can be stored at room temperature for long periods of time.

An object of the invention is to provide a controlled transfer of a biological sample to a dry, treated solid storage and transfer medium, such as providing a reproducible pressure or movement between the analyte collection surface and the storage medium.

A second object of the invention is to provide a device or method that has a spare sample source in sample retained in an absorbent analyte collection surface.

A third object of the invention is to provide a device or method that retains the sample collector surface and the storage medium together for chain of custody traceability purposes.

A fourth object of the invention is to provide a device or method in which the storage medium can be processed by automated analyzing methods.

A fifth object of the invention is to provide a device or method for the long term storage for biological samples.

BRIEF DESCRIPTION OF THE DRAWINGS

FIG. 5 is a perspective view of a further embodiment of the present invention showing the claimed element in an open position;

FIG. 6 is a perspective view of a further embodiment of the present invention showing the claimed element in a closed position;

DETAILED DESCRIPTION OF THE INVENTION

Figure 1:
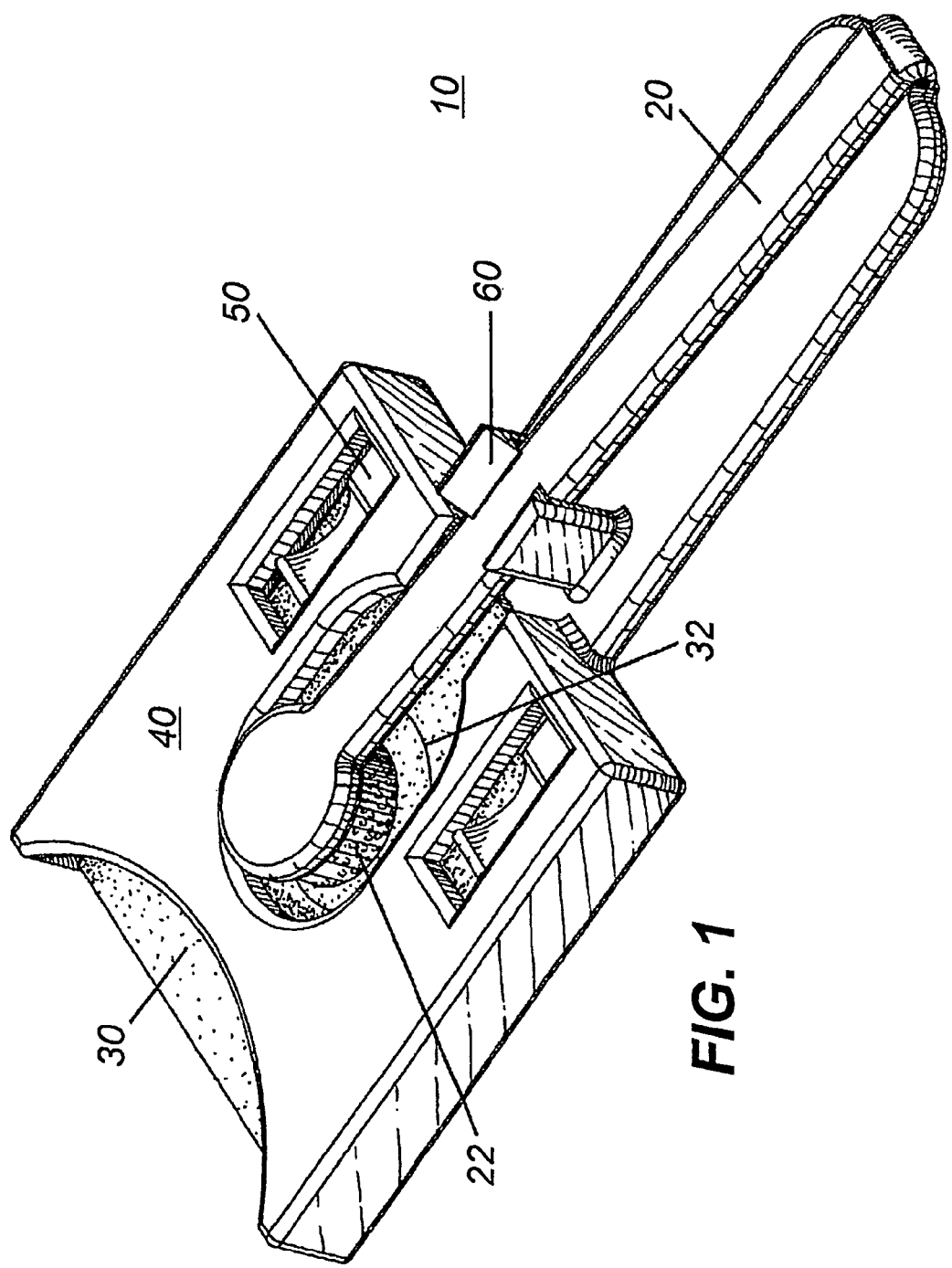
FIG. 1 is a perspective view of a preferred embodiment of the present invention showing the claimed element in a closed position.
Figure 2:
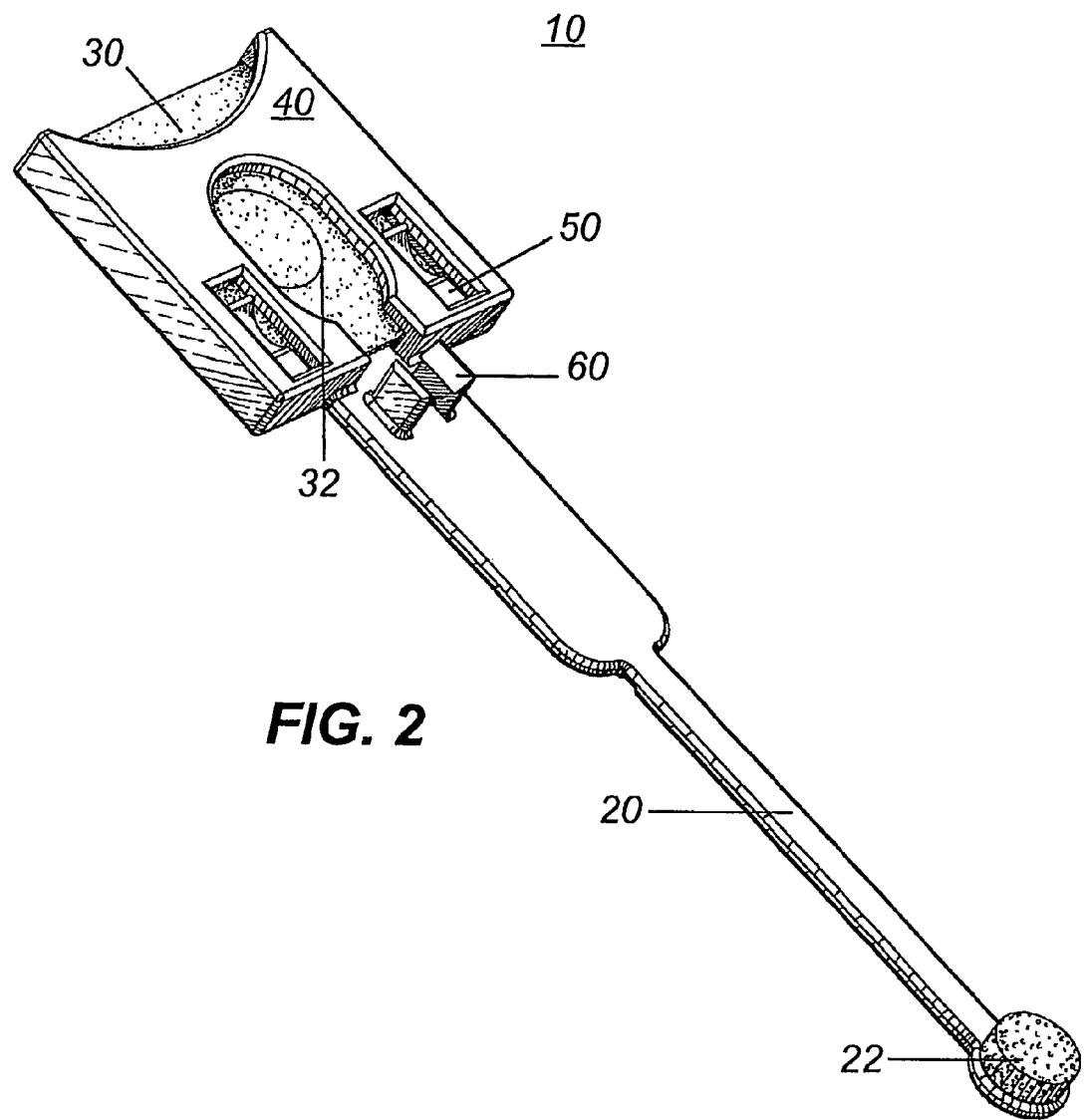
FIG. 2 is a perspective view of a preferred embodiment of the present invention showing the claimed element in an open position.
Figure 3:
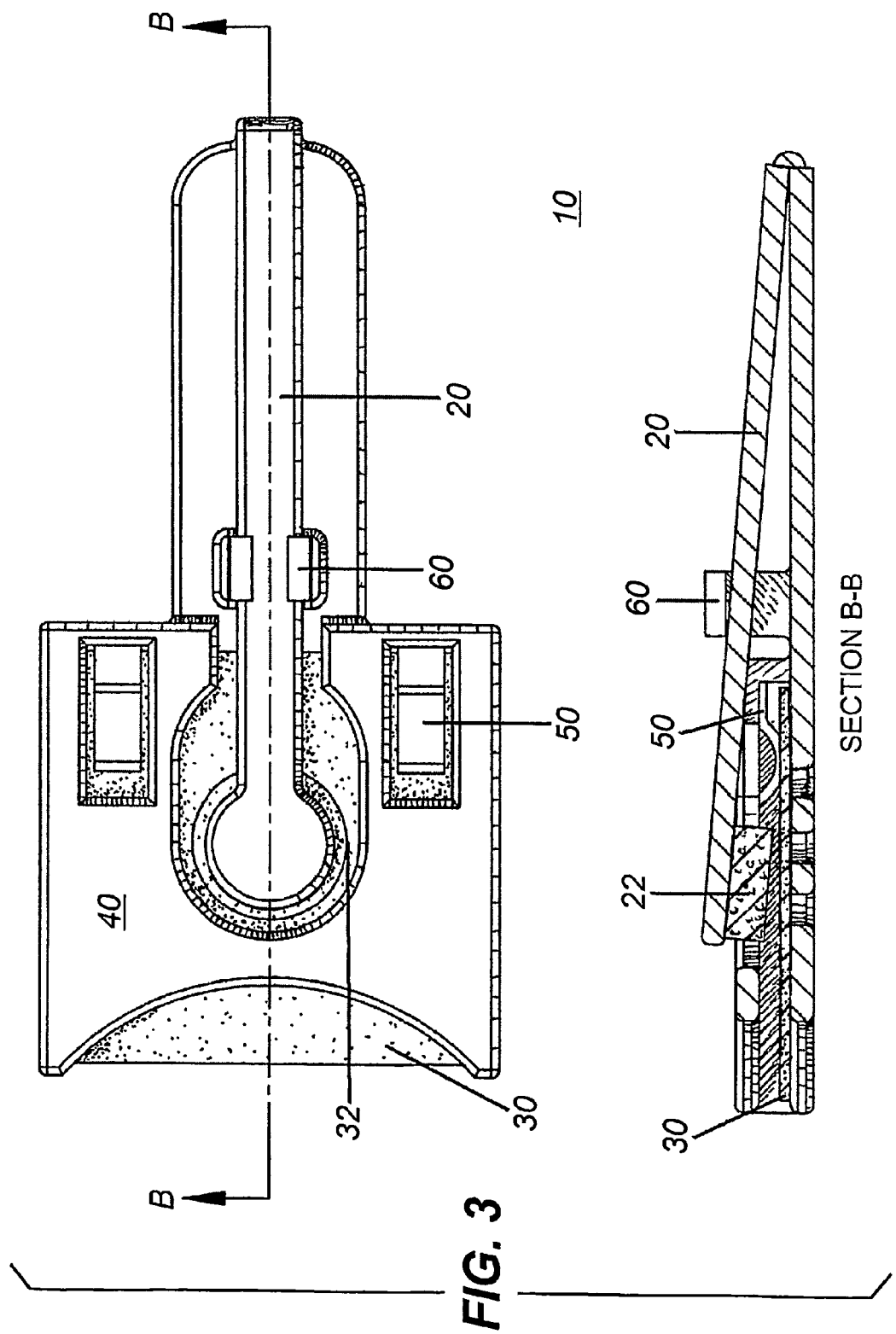
FIG. 3 is a plan and sectional view of the FIG. 1 device.
Figure 4:
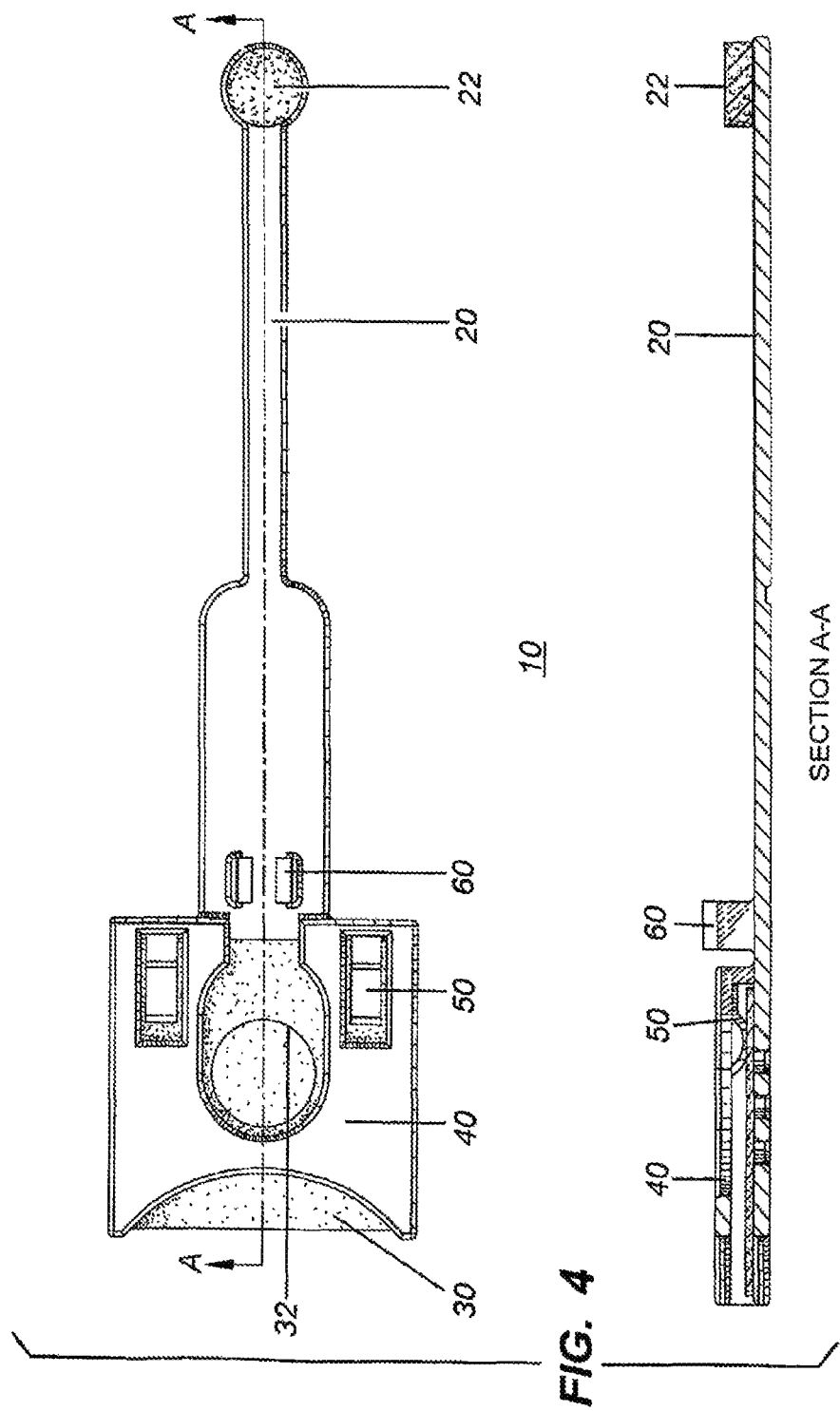
FIG. 4 is a plan and sectional view of the FIG. 2 device.

A preferred embodiment is shown in FIG. 1. The collection device (10) for a biological sample that contains degradable biologically sourced analytes comprises a moveable sample collection member (20) having an analyte collection surface (22), a storage medium (30), and a storage medium holder (40) having a means for holding the storage medium in a fixed position (50) and a means for holding the moveable sample collection member (60). The moveable sample collection holding means allows the moveable collection member surface to move either from a first closed position facing or contacting at least a portion of the storage medium (as shown in FIGS. 1 and 3) to a second open position for collecting the biological sample on the analyte collection surface (as shown in FIGS. 2 and 4) or vice versa.

Preferably, the means for holding the moveable sample collection member comprises a unitary connection between the storage medium holder and the moveable sample collection member (as shown in the FIGURES). Also preferably, the moveable sample collection surface is dimensioned and configured to be in spring tension away from the storage medium surface when held by the member holding means such that the analyte collection surface is held off the storage medium thereby allowing enough space for air drying of the storage medium after transfer of the sample to the storage medium from that surface.

Preferably the storage medium will also comprise at least one stabilizing reagent that preserves at least one biological sample analyte for transport or storage. Suitable such reagents include either the combination of a weak base, a chelating agent, and, optionally, uric acid or a urate salt or simply the addition of a chaotropic salt, alone or in combination with a surfactant.

The "weak base" of the composition may be a Lewis base which has a pH of about 6 to 10, preferably about pH 8 to 9.5. One function of the weak base is to act as a buffer to maintain a composition pH of about 6 to 10, preferably about pH 8.0 to 9.5, for example, pH 8.6. Hence, a weak base suitable for the composition of the invention may, in conjunction with other components of the composition, provide a composition pH of 6 to 10, preferably, about pH 8.0 to 9.5. Suitable weak bases according to the invention include organic and inorganic bases. Suitable inorganic weak bases include, for example, an alkali metal carbonate, bicarbonate, phosphate or borate (e.g., sodium, lithium, or potassium carbonate). Suitable organic weak bases include, for example, tris-hydroxymethyl amino methane (Tris), ethanolamine, triethanolamine and glycine and alkaline salts of organic acids (e.g., trisodium citrate). A preferred organic weak base is a weak monovalent organic base, for example, Tris. The Tris may be either a free base or a salt, for example, a carbonate salt.

A preferred chelating agent is a strong chelating agent. By "strong" chelating agent it is meant that the agent binds multivalent metal ions with a comparable or better affinity than ethylene diamine tetraacetic acid (EDTA). A preferred chelating agent according to the invention is EDTA.

Anioinic surfactants are examples of surfactants which are useful in the present invention. A preferred anionic detergent is a strong anionic detergent. As used herein, a "strong" anionic detergent includes a hydrocarbon moiety, aliphatic or aromatic, containing one or more anionic groups. Particularly preferred anionic detergents suitable for the invention include sodium dodecyl sulphate (SDS) and sodium lauryl sarcosinate (SLS). In a preferred embodiment, the anionic detergent causes inactivation of most microorganisms which have protein or lipids in their outer membranes or capsids, for example, fungi, bacteria or viruses. This includes microorganisms which may be pathogenic to humans and are present in a biological sample.

Also preferably, the storage medium will have a visual delineation (32) placed around the transfer area of the storage medium such that if removed from the storage holding means an operator can know where the material was deposited without reference to the device.

The present device can be used to collect degradable biologically sourced analytes such as nucleic acids, proteins, and respective fragments thereof. The biological sample can be selected from the group consisting of saliva, blood, serum, lymph fluids, buccal cells, mucosal cells, cerebrospinal fluid, semen, vaginal fluid, feces, plasma, urine, a suspension of cells, or a suspension of cells and viruses.

Preferably, the present device is dimensioned and configured such that the storage medium holder (40) releaseably holds the storage medium (30) in the fixed position by the holding means (50) (such as the plastic arms shown in the FIGURES). Thus, one can separate the storage medium from the storage holder for subsequent processing or storage. The tension on the storage medium should allow for manual or automated extraction, but not allow for accidental loss of the storage medium from the device.

As described above, the means for holding the moveable sample collection member may comprise a resilient member (70) positioned on the storage medium holder. This is illustrated in FIG. 5. In use, where the moveable sample collection member is moved to a closed position, the resilient member on the storage medium holder engages the moveable collection member and releasably holds it in a fixed position such that the surface thereof is in contact with the storage medium, thereby maintaining a uniform and constant pressure between the moveable collection member surface and the storage medium.

In some cases, one can dimension and configure the storage medium holder so as to expose at least a portion of the storage medium for removal of the storage medium from the storage medium holder.

Preferably, the analyte collection surface (22) comprises an absorbent material, such as a conventional porous polyurethane foam pad (from Powell Products, Inc. of Colorado Springs, Colo. USA), that is suitable for collecting a biological sample. Examples of other suitable absorbent materials include hydrophilic non-reticulated, closed cell foams, hydrophilic, non-reticulated, open cell foams, hydrophobic non-reticulated closed cell foams, hydrophobic non-reticulated open cell foams, hydrophobic reticulated open cell foams, absorbent gel materials used for transfers and cotton based absorbent material. The analyte collection surface should be dimensioned and configured such that the volume of sample is controlled. By controlling the volume, any stabilizing reagents on the storage medium are not overloaded in their respective protecting capacity. If used in buccal swab applications, the pad should be dimensioned and configured to fit within the human mouth.

For record keeping and traceability the present device should also comprise an identification label (such as conventional bar coding) on not only the storage medium, but also the collection member, and if not unitary, the storage medium holder as well.

To ensure device integrity, the present device can also comprise a sterility envelope surrounding the other device elements. Preferably, those other elements are sterile and free from any biological sample analytes (made for example, from medical grade plastics), which can be done through conventional techniques such as irradiation after the envelope is sealed.

Kits can be made that incorporate the above device along with any combination of associated equipment or reagents including purification reagents, buffers, or the like and storage systems, containers, or the like.

In this regard, the present invention further provides a kit comprising a device as defined herein and one or more components selected from the group consisting of purification reagents for subsequent analysis of the sample, buffers, storage systems and containers.

Example of Device Use

The present device can be used for biological sample collection for the following purposes: the collection of buccal cell samples for criminal databases; the collection of crime scene samples (i.e., rehydrated blood, semen, saliva and liquid samples of the same); the collection of sexual assault samples; the collection of buccal samples for population genetics or pharmacogenomics studies; the collection of buccal samples for personal genetic ID archiving; the collection of bacterial or parasite samples from food sources; the collection of blood from meat at slaughterhouse for meat traceability; or the collection of biological samples from animals for veterinary diagnostics.

EXAMPLES

Example 1

Cell Transfer Assays

Cell transfer assays were performed in order to evaluate the transfer efficiency of the device of the present invention. The device used in each of these experiments was a device as illustrated in FIG. 5. The analyte collection surface was formed from foam (Aquazone® available from Reilly Foam Corporation, Pa., USA) and the storage medium comprised FTA filter paper (obtained from Whatman, Inc., N.J., USA).

THP-1 cultures were grown to densities of $10^6$ cells/ml, centrifuged and subsequently resuspended at a concentration of $10^7$ cells/ml. A serial dilution of this stock was performed to give concentrations of $10^5$, $10^4$ and $10^3$ cells/ml. Each of these dilutions was applied to the foam collection surface of a device according to the present invention (100 µl each); the devices were then closed and clipped in place for 10 seconds before release of the applicator foam to the resting position.

2 mm discs were punched from the white application area of the pink indicator FTA filter paper card and placed into 0.5 ml tubes with 200 µl FTA Purification Reagent. Following a five minute incubation at room temperature, the tubes were finger-flicked for 10 seconds. Liquid was removed and the wash step repeated two more times for a total of three washes with FTA Purification Reagent. TE buffer (200 µl) was added to each tube, incubated for 5 minutes at room temperature, and the TE was removed and discarded. This was repeated for a total of two washes using TE buffer, after which the disc was dried for 1 hour at room temperature.

PCR amplification of the β-globin gene and capillary electrophoresis were then performed. Analysis was performed using β-globin PCR assays via Exeprion Bioanalyzer 1K DNA chips. DNA detection was defined as the presence of β-globin amplicons on the Experion 1K Chips with a detection limit at 0.1 ng/µl.

Figure 7:
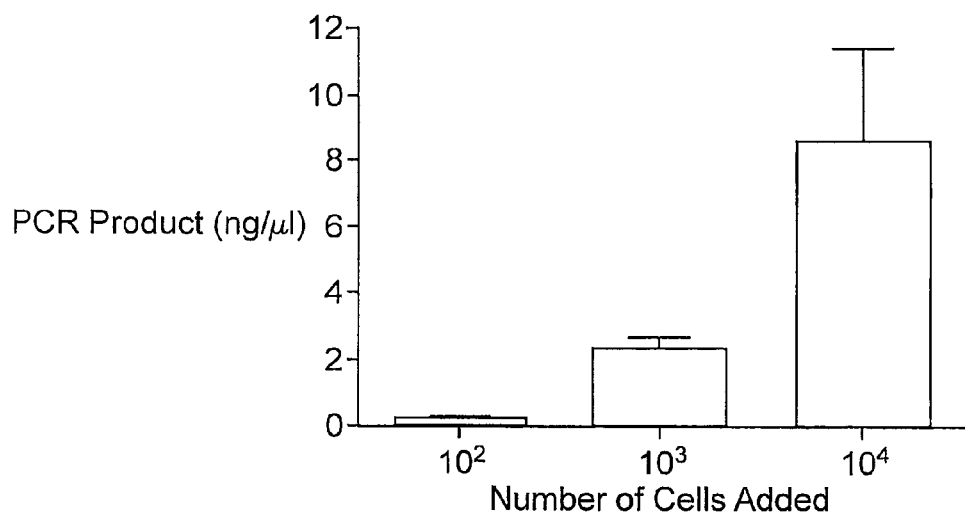
FIG. 7 is a graph illustrating the PCR product concentrations obtained from β-globin PCR amplifications following use of THP-1 cells in a device of the present invention.

The results obtained are set out in FIG. 7 which illustrates that detectable amplification was observed using all concentrations of cells. More specifically, PCR product was successfully detected even following application of only 100 cells to each device. Excellent results were obtained where 1000 cells were applied to the applicator foam to yield β-globin PCR amplicon concentrations ranging from 1.5 to 3.2 ng/µl.

Example 2

Buccal Cell Mapping Experiments

Samples were collected from four subjects, each using two devices as illustrated in FIG. 5. The samples were collected according to the following protocol:

a) Holding the plastic stem above the hinge joint, the foam tip of the device was placed in the mouth of the subject and the foam analyte collection surface was rubbed on the inside of the cheek for 15 seconds. This procedure was repeated using the opposite cheek. The foam analyte surface was rubbed along the gum-line, at the fold line of the cheek and under the tongue, soaking up as much saliva as possible. The foam analyte surface was then removed from the mouth.

b) The protective film of the storage medium was removed, exposing the FTA Card storage medium.

c) The device was folded at the hinge joint and the foam analyte surface was pressed onto the FTA Card making sure that the foam sample collection surface was held in place by the clip at the front of the FTA Card holder. The device was then closed and the sample collection member was pushed into the lowest position on the clip. The device was left in this position for 10 seconds.

d) Whilst holding the FTA Card holder, the device handle was bent back to release the foam sample collection surface from the clip and to pull the sample collection member up to the top position on the clip. The device was bent to lift the foam sample collection surface from the FTA Card storage medium.

e) The FTA card storage medium was removed and dried for 3 hours, ready for subsequent analysis.

Figure 8A:
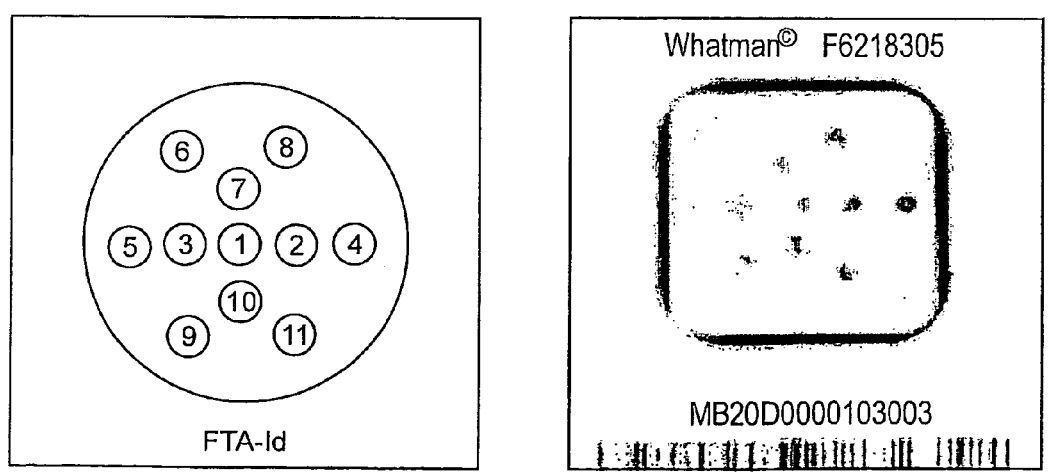
FIG. 8a is a punch map showing the buccal cell application area after transfer of buccal cells using a device according to the present invention.
Figure 8B:
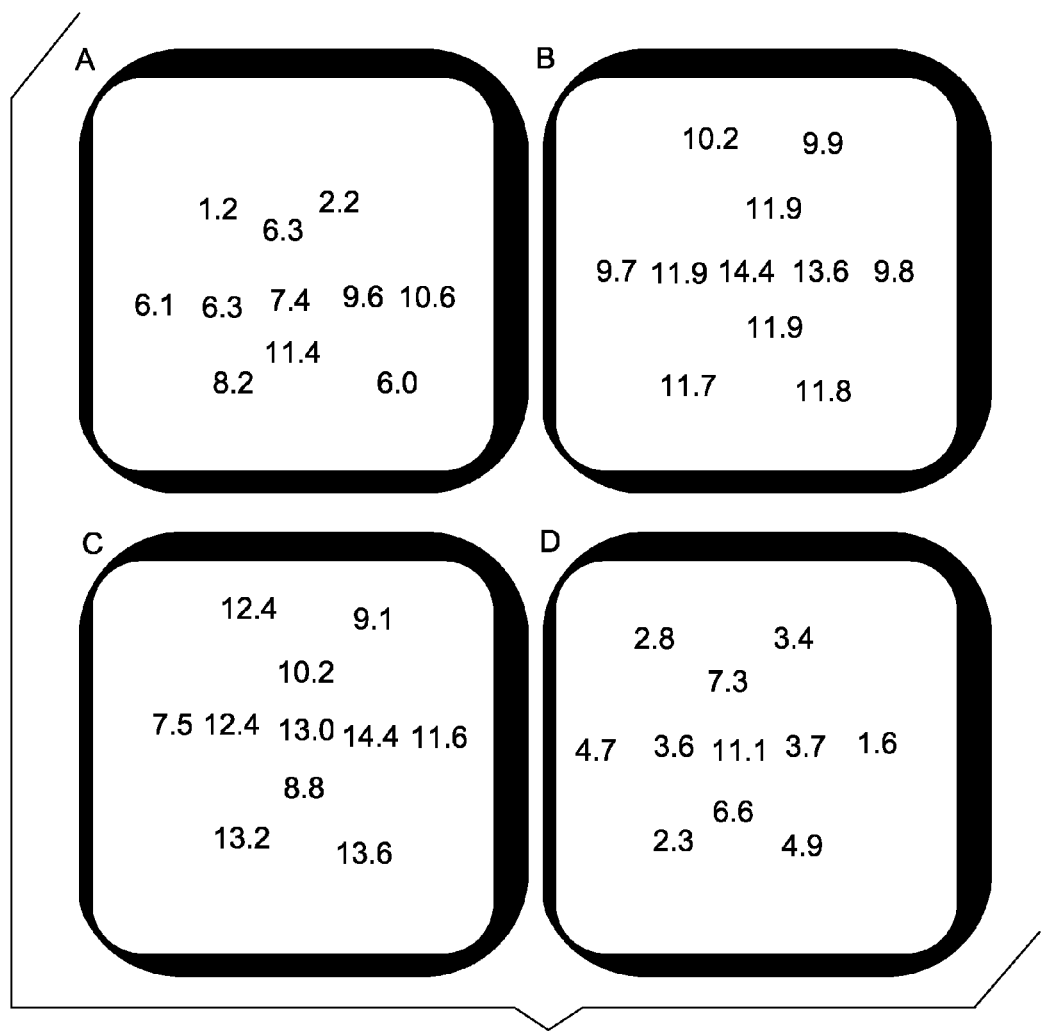
FIG. 8b illustrates the distribution of buccal cells on the storage medium using the method of the present invention.

Eleven discs (2.0 mm diameter) were punched from each card as shown in FIG. 8a, and PCR amplifications targeting a 268 bp portion of the β-globin gene were completed and are shown in FIG. 8b. The amplicons were quantified using an Experion analyzer (Bio-Rad) and are shown graphically in FIG. 8c as a Box and Whiskers Plot. A total of 88 punches were analyzed from eight Indicating FTA cards; 87 contained sufficient DNA template for successful PCR, i.e. only 1 failure in 88 punches (in this case, the failed punch was taken from the periphery of the application area). Negative controls included paper-only samples (devoid of biological sample) and water only (no template PCR). In both negative control cases, amplification of PCR products was not detected.

With reference to FIG. 8a, the punch maps show the buccal cell application area after transfer of buccal cells from the foam applicator to the Indicating FTA card (storage medium) using the device of the present invention. Eleven 2 mm punches were removed from each card as shown in FIG. 8a. The large circle represents the typical area of cell transfer indicated by a change in Indicating FTA color from pink to white.

With reference to FIG. 8b, the concentration of DNA detected is directly proportional to the number of buccal cells transferred to the FTA card. Four different donors used device of the present invention to harvest buccal cells from inside their cheeks and transfer them to Indicating FTA cards for analysis. Panels A-D show DNA distribution maps of DNA on the FTA card after transfer of cells from the devices. Each data point represents the yield of PCR amplicons (ngs) produced from the β-globin amplification of DNA present on a 2 mm disk. The PCR amplification was quantified using the Experion Bioanalyzer. The distribution of DNA present on the cards indicates that the transfer of cells was consistently uniform.

Figure 8C:
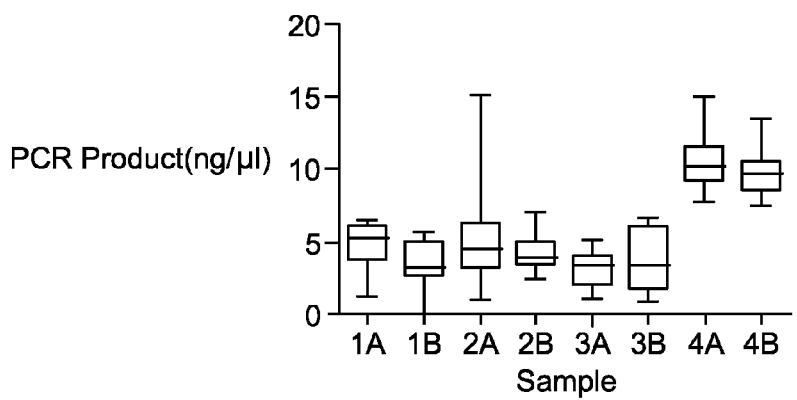
FIG. 8c is a box and whisker plot of PCR product concentrations obtained after β-globin PCR amplifications from 11 discs punched from each FTA storage medium.

With reference to FIG. 8c, the range is shown as the whiskers and the box shows the area where 50% of the data points lie. The bar in the box represents the median value for the 11 data points. The data shown in the Box and Whiskers Plot indicates that the transfer of buccal cells from the sample collection surface to the storage medium was consistent. Sample 1B contains a single failed PCR reaction; the only one out of 88 PCR amplifications. Sample 2A contained a single outlier point that skewed the upper range of PCR yields, and this is likely the result of a cell-clump transferred to the FTA card. PCR products showed minor variation in concentration within an individual set, but the variation is most notable between subjects; for example subject #4 harvested substantially more cells than other subjects on both collection devices used. This serves to underscore the differences in shedding buccal cells from one person to the next.

Figure 9A:
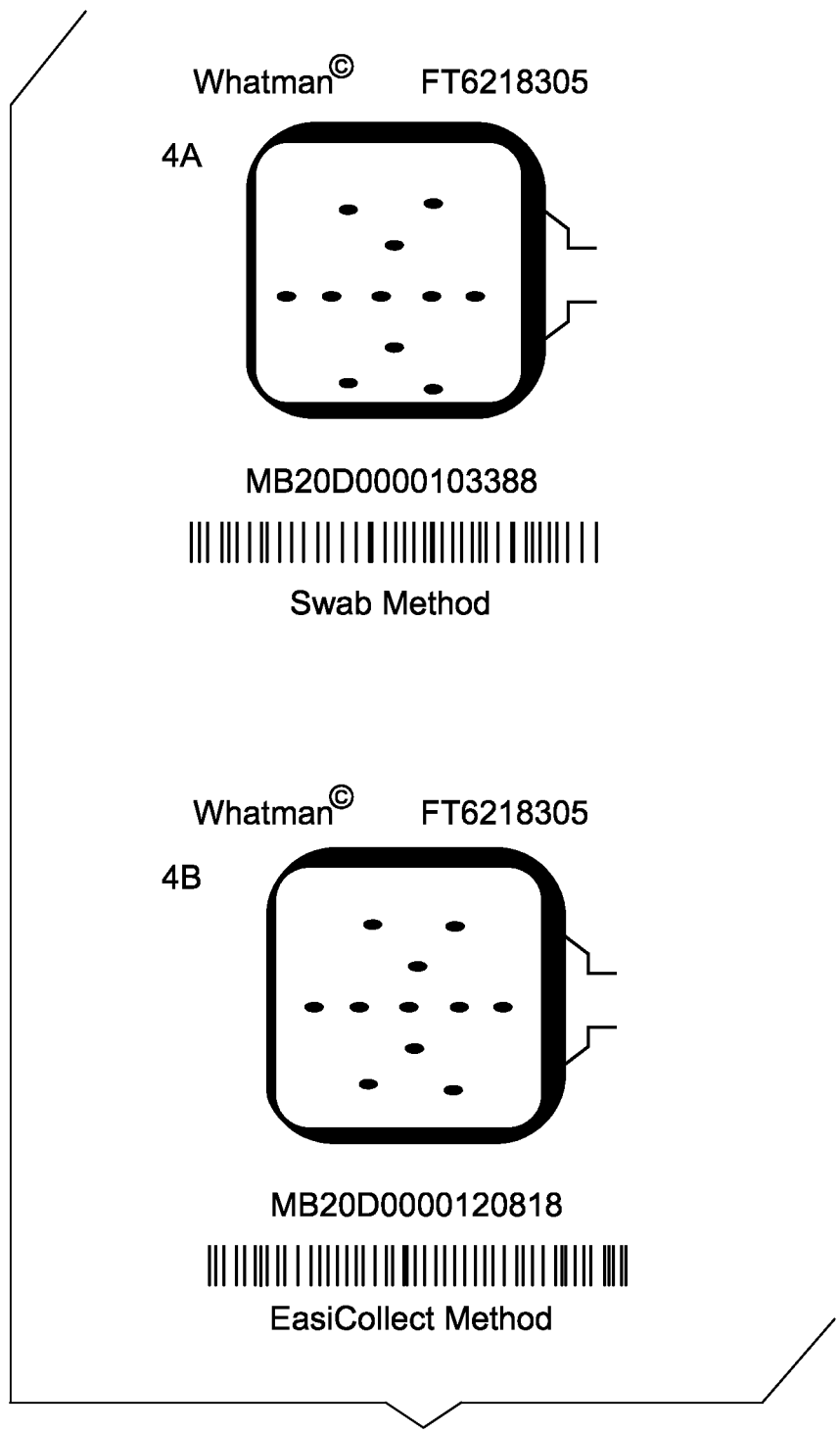
FIG. 9a is a comparison of the transfer patterns obtained using the method of the present invention and the traditional swab method.
Figure 9B:
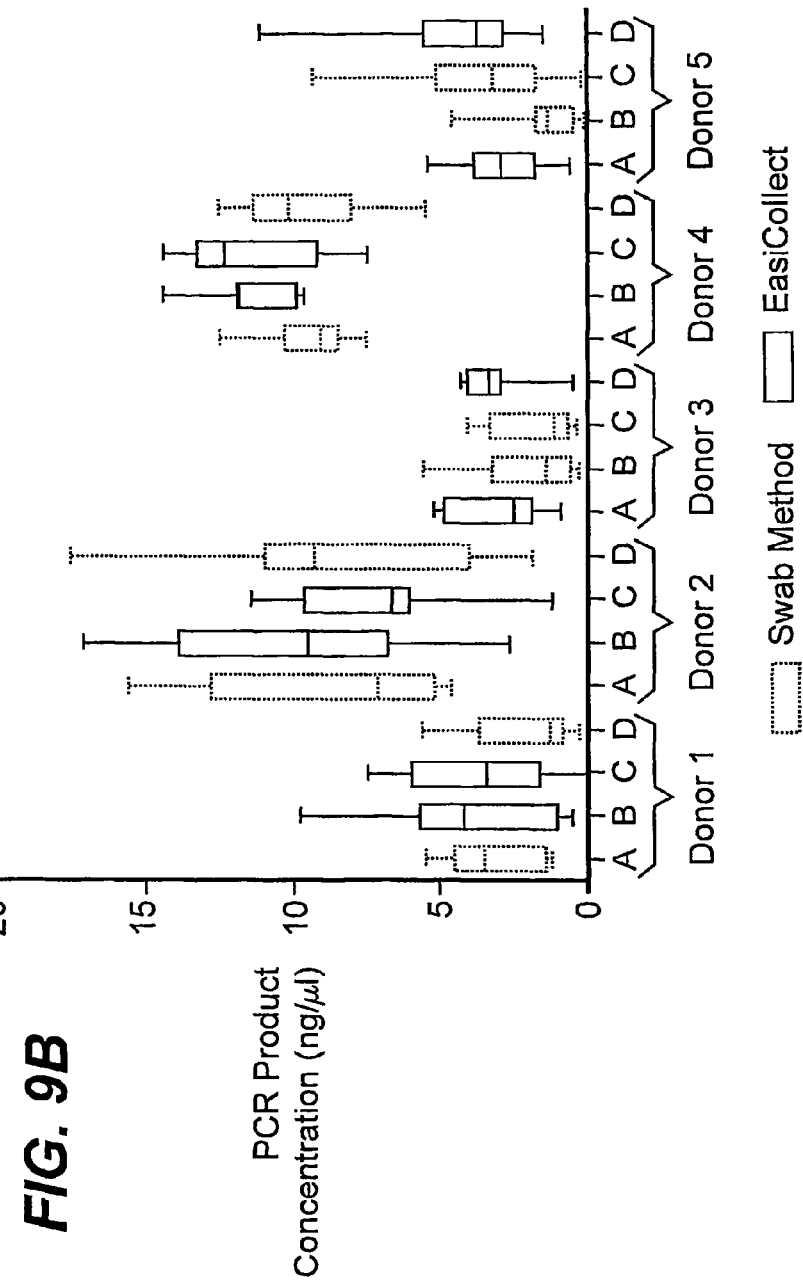
FIG. 9b is a comparison between the method of the present invention and swab methods for the collection of buccal cells from five different donors.

The final set of experiments utilizing buccal cell maps are displayed in FIGS. 9a and 9b, respectively. These figures show the results of a comparative analysis of the method of the present invention against the traditional swab method of buccal cell collection. Five buccal cell donors collected two buccal cell FTA cards using the method described above and two cards using the traditional swab method. The protocol for cell collection identified above was followed except that the swab was rolled onto the FTA card (storage medium).

Each donor was sampled a total of four times (A-D), using two devices of the invention and two swabs. To remove sampling order bias, the collection method order was varied between individuals in the order shown in FIG. 9b (A=$1^{st}$ to D=$4^{th}$). Following sample collection, FTA cards were processed using standard protocols as described above and PCR was performed to amplify a fragment of the β-globin gene from 11 positions within the application area as described above. Resultant PCR products were quantified using an Experion Bioanalyzer.

The comparison of performance between the device of the present invention and the traditional swab method reveals that the present method provides for a well defined area of buccal cell transfer while the swab produces variable transfer patterns that require the user to make a "best guess" of where to collect a punch sample (FIG. 9a). The device of the present invention provides a well defined application area making automated punching more accurate. The Box and Whiskers Plot in FIG. 9b shows that the method using the device of the present invention consistently collects higher yields of buccal cells and generates a more uniform transfer of cells than does the swab method regardless of the order in which samples were collected.

Example 3

STR Analysis

Buccal samples utilized for STR analysis were taken from the same collection devices in Example 2 above. Two 1.2 mm punches were collected from central locations of each Indicating FTA card storage medium. All punches were washed and dried following the protocol outlined in Example 1.

STR analysis was performed using the Promega PowerPlex 16® system following the manufacturer's instructions. A processed and dried Indicating FTA punch was used in each PCR reaction as a method of direct amplification from the punch. PCR was carried out on an Applied Biosystems 7900HT, and PCR products were visualized on an Applied Biosystems 310 Genetic Analyzer. Analysis of products was carried out with GeneMapper 3.2® software.

Figure 10:
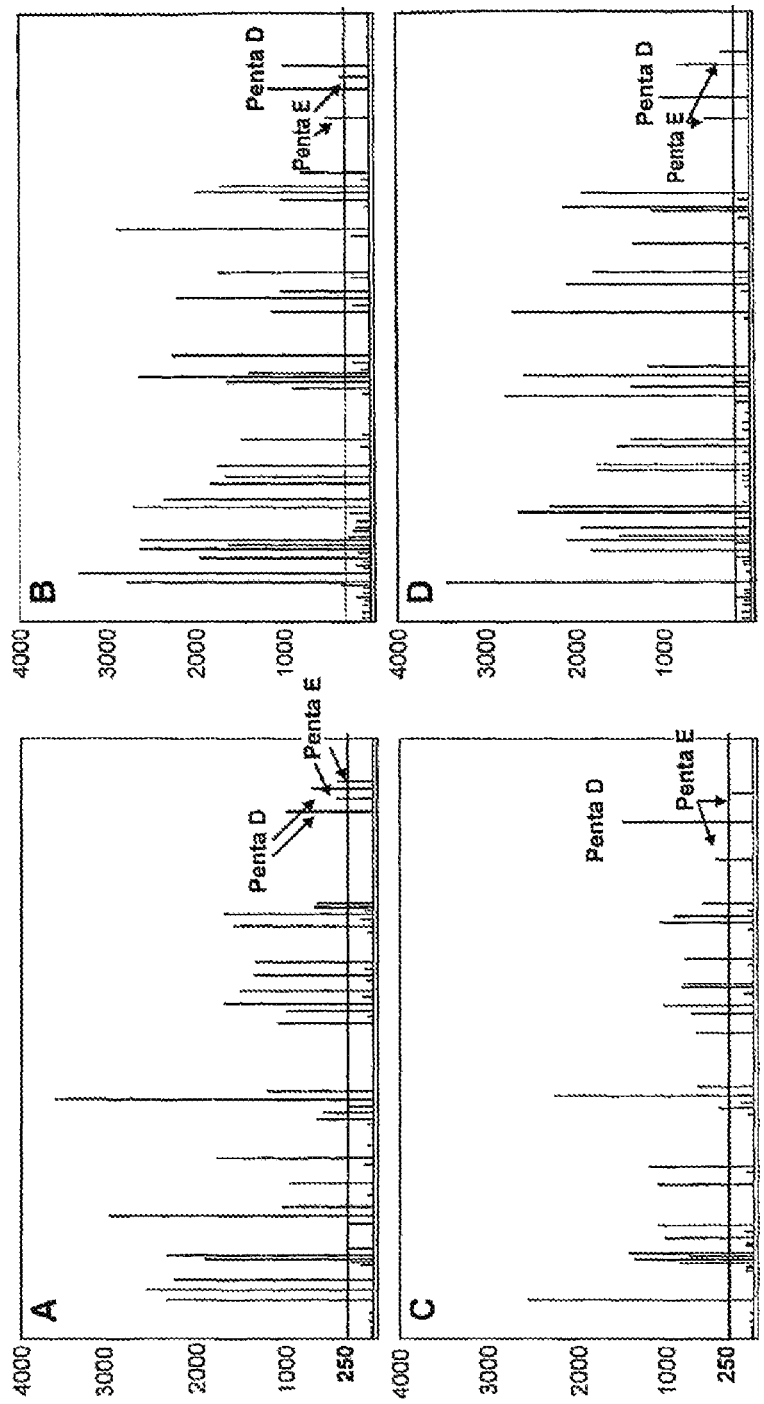
FIG. 10 shows the results of an STR analysis of four donor individuals using Promega PowerPlex 16.

All 4 sets of buccal collection produced excellent quality results for all 16 alleles above 250 RFU's (relative fluorescent units) as seen in FIG. 10. This exceeds the desired criterion from the Design Input document of 200 RFU's. Although, there was some minor variation in the intensity of the peaks, the peak balance and peak intensity remained well within the GeneMapper software acceptable parameters. As expected, replicate devices from the same individual produced the same allelic profile. Allelic profiles are found in Table I. A series of 50 samples were collected with the device of the present invention, processed and analyzed using Promega's PowerPlex 16 system of STR analysis (Table 2).

quality is excellent with peak balance running 85% to 100%, well above the acceptable range of 60% for accurate allele calls.

We claim:

1. A method for collecting a biological sample that contains degradable biologically sourced analytes comprising:
   a) obtaining a device comprised of
      i) a sample collection member having an analyte collection surface in the form of a pad of material mounted to an elongated stem that extends in a longitudinal direction;
      ii) a sample storage medium wherein the sample storage medium comprises at least one stabilizing reagent that preserves at least one biological sample analyte for transport or storage; and
      iii) a storage medium holder having one or more retention arms and a means for pressing the pad onto the sample storage medium, for transfer of at least a portion of the biological sample onto the sample storage medium,
      iv) wherein the sample collection member is configured to be moveable between at least two positions including a first position in which the pad of material is spaced from the sample storage medium in the longitudinal direction and a second position where the pad of material is in contact with the sample storage medium,
      v) wherein the sample storage medium is slidably insertable into the storage medium holder in a direction generally parallel to an interface formed between the pad of material and the sample storage medium when the pad of material is in the second position, and
      vi) wherein the one or more retention arms are configured to removably hold the sample storage medium in a position by exerting a force on the sample storage medium;

TABLE 1

|         | D3S1358 | TH01  | D21S11 | D18S51 | Penta_E | D5S818 | D13S317 | D7S820 |
|---------|---------|-------|--------|--------|---------|--------|---------|--------|
| Donor 1 | 17      | 6/9.3 | 28/29  | 13/15  | 12/14   | 8/11   | 12      | 10/11  |
| Donor 2 | 14/16   | 7/8   | 30/31  | 17     | 7/12    | 10/11  | 8/12    | 10/11  |
| Donor 3 | 16/17   | 9.3   | 30/31  | 12/16  | 5/13    | 11/12  | 11      | 11/12  |
| Donor 4 | 15/17   | 9/9.3 | 29/30  | 15/20  | 7/15    | 11/13  | 11/12   | 8/12   |

|         | D16S539 | CSF1PO | Penta_D | AMEL | vWA   | D8S1179 | TPOX | FGA    |
|---------|---------|--------|---------|------|-------|---------|------|--------|
| Donor 1 | 11/13   | 10/12  | 10/13   | X/Y  | 18    | 13      | 9/11 | 22/22.3|
| Donor 2 | 9/13    | 12/13  | 10/13   | X/Y  | 17/18 | 14/17   | 8/11 | 20/24  |
| Donor 3 | 11/14   | 11/12  | 9       | X    | 15/17 | 14      | 8/11 | 21/23  |
| Donor 4 | 11/13   | 10/12  | 9/13    | X    | 16/17 | 11/14   | 8    | 19/21  |

TABLE 2

| Promega's PowerPlex 16 STR System | number of samples | Amelogenin | CODIS alleles | Penta D & E | Totals |
|---|---|---|---|---|---|
| Total possible allele calls | 50 | 50 | 650 | 100 | 800 |
| Total correct allele calls* | 49 | 49 | 642 | 98 | 789 |
| Total failed allele calls | 1 | 1 | 8 | 2 | 11 |
| Re-run of failed sample correct allele calls** | 1 | 1 | 13 | 2 | 16 |
| Total Correct Allele calls after sample re-run | 50 | 50 | 650 | 100 | 800 |
| % accuracy after first set of injections | | | | | 98.6% |
| % accuracy after failed sample re-run | | | | | 100% |

*all allele calls of peaks with ≥200 RFU
**10 second reinjection of sample; peak balance was <60% for several heterozygous peaks In FIG. 10, A, B, C, and D are results from buccal cell donors 1, 2, 3, and 4 respectively. The red line indicates the point of 250 rfu's. Both Penta D and E alleles are marked as indicators for DNA template quality since they are typically the first alleles to fail when it is compromised resulting in allele drop-out. In the electropherograms below, the template b) collecting a biological sample on the pad;
c) moving the sample collection member between at least two positions, including the first position and the second position, while the one or more retention arms hold the sample storage medium in position
d) operating the storage medium holder to press the pad onto the sample storage medium;
e) releasing the pad from the sample storage medium; and
f) removing the sample storage medium from the storage medium holder.

2. The method of claim 1, wherein the method includes providing a visual delineation at an area of the sample storage medium where transfer of the sample takes place.

3. The method of claim 1, wherein the means for pressing the pad onto the sample storage medium provides a reproducible pressure between the pad and the sample storage medium during the step of operating the storage medium holder to press the pad onto the sample storage medium and before the step of releasing the pad from the sample storage medium.

4. A device for collecting a biological sample that contains degradable biologically sourced analytes, the device comprising:
   i) a sample collection member having an analyte collection surface in the form of a pad of material mounted to an elongated stem that extends in a longitudinal direction;
   ii) a sample storage medium wherein the sample storage medium comprises at least one stabilizing reagent that preserves at least one biological sample analyte for transport or storage; and
   iii) a storage medium holder having one or more retention arms and a means for pressing the pad onto the sample storage medium, for transfer of at least a portion of the biological sample from the pad onto the sample storage medium and for then releasing the pad from the sample storage medium,
   iv) wherein the sample collection member is configured to be moveable between at least two positions, including a first position in which the pad of material is spaced from the sample storage medium in the longitudinal direction, and a second position where the pad of material is in contact with the sample storage medium,
   v) wherein the storage medium holder is configured to enable the sample collection member to be moved between the first and second positions while the one or more retention arms hold the sample storage medium in position, and
   vi) wherein the sample storage medium is slidably insertable into the storage medium holder in a direction generally parallel to an interface formed between the pad of material and the sample storage medium when the pad of material is in the second position, and
   vii) wherein the one or more retention arms are configured to removably hold the sample storage medium in a position by exerting a force on the sample storage medium.

5. A device including a stabilizing reagent for collecting a biological sample that contains degradable biologically sourced analytes, the device comprising:
   i) a sample collection member having an analyte collection surface in the form of a pad of material mounted to an elongated stem that extends in a longitudinal direction, and being configured to be moveable between a first position and a second position;
   ii) a sample storage medium comprising the stabilizing reagent that preserves the biological sample for transport or storage, wherein in the first position the pad of material is spaced from the sample storage medium in the longitudinal direction and in the second position the pad of material is in contact with the sample storage medium; and
   iii) a storage medium holder configured to hold the sample storage medium in a fixed position and press the pad onto the sample storage medium, for transfer of at least a portion of the biological sample from the pad onto the sample storage medium and for then releasing the pad from the sample storage medium,
   iv) wherein the storage medium holder is configured to enable the sample collection member to be moved between the first and second positions while the storage medium holder holds the sample storage medium in the fixed position, and
   v) wherein the sample storage medium is slidably insertable into the storage medium holder in a direction generally parallel to an interface formed between the pad of material and the sample storage medium when the pad of material is in the second position, and
   vi) wherein the storage medium holder comprises one or more retention arms configured to removably hold the sample storage medium in a position by exerting a force on the sample storage medium.

6. The device of claim 5, wherein the storage medium holder further comprises an arm that releasably holds the sample storage medium in the fixed position.

7. The device of claim 5 further comprising a resilient member to releasably hold the sample collection member in the second position.

* * * * *